United States Patent [19]
Barton et al.

[11] Patent Number: 5,695,745
[45] Date of Patent: Dec. 9, 1997

[54] ORAL HYGIENE COMPOSITION

[75] Inventors: Stephen Peter Barton; Edward Galley, both of Nottingham, England

[73] Assignee: The Boots Company PLC, Nottingham, United Kingdom

[21] Appl. No.: 416,841
[22] PCT Filed: Oct. 12, 1993
[86] PCT No.: PCT/EP93/02812
  § 371 Date: Apr. 13, 1995
  § 102(e) Date: Apr. 13, 1995
[87] PCT Pub. No.: WO94/08559
  PCT Pub. Date: Apr. 28, 1994

[30] Foreign Application Priority Data
Oct. 14, 1992 [GB] United Kingdom ............. 9221593

[51] Int. Cl.⁶ .................. A61K 7/16; A61K 7/22
[52] U.S. Cl. ...................... 424/49; 424/54; 424/57
[58] Field of Search ........................ 427/49–58

[56] References Cited

U.S. PATENT DOCUMENTS

| | | | |
|---|---|---|---|
| Re. 32,300 | 12/1986 | Gorman et al. | 514/635 |
| 3,976,765 | 8/1976 | Nachtigal | 424/54 |
| 4,130,637 | 12/1978 | Bauman | 424/54 |
| 4,311,618 | 1/1982 | Schafer-Burkhard | 252/542 |
| 4,323,551 | 4/1982 | Parran, Jr. | |
| 4,420,484 | 12/1983 | Gorman et al. | 424/326 |
| 4,976,954 | 12/1990 | Kleber et al. | 424/52 |
| 5,064,640 | 11/1991 | Kleber et al. | 424/52 |
| 5,158,763 | 10/1992 | Gaffar et al. | 424/54 |
| 5,180,577 | 1/1993 | Polefka et al. | 424/52 |
| 5,316,758 | 5/1994 | Morishima et al. | 424/54 |
| 5,449,763 | 9/1995 | Wulff et al. | 536/18.6 |

FOREIGN PATENT DOCUMENTS 0480812  4/1992  European Pat. Off. .

*Primary Examiner*—Shep K. Rose
*Attorney, Agent, or Firm*—Nikaido, Marmelstein, Murray & Oram LLP

[57] ABSTRACT

An oral hygiene composition comprises a cationic antimicrobial agent (such as chlorhexidine gluconate), an anionic active agent (such as an alkali metal pyrophosphate) and both a non-ionic surfactant having a high hydrophilic/lipophilic balance (such as an ethoxylated castor oil) and an amphoteric surfactant (such as cocoamidopropyl betaine).

13 Claims, No Drawings

ORAL HYGIENE COMPOSITION

The present invention relates to an oral hygiene composition having antimicrobial action. The invention relates in particular to a stabilised composition comprising both a cationic antimicrobial agent and an anionic anticalculus and/or antistaining agent, and to methods for use of such a composition.

The term 'oral hygiene composition' as used herein includes inter alia dentifrices, mouthwashes, toothpowders, chewing gums and lozenges and denture cleansing formulations. Mouthwashes are particularly preferred.

Oral hygiene compositions containing cationic antimicrobial agents are well-known in the art. Such antimicrobial agents are known to be effective to reduce levels of plaque in the mouth.

Separate oral hygiene compositions comprising anionic anticalculus agents are also known. For example, U.S. Pat. No. 4,515,772 (Parran) describes an oral hygiene composition in the form of a mouthwash, liquid dentifrice or toothpaste which comprises an anionic anticalculus agent in the form of a water-soluble alkali-metal pyrophosphate.

However, many prior art compositions comprising both cationic antimicrobial agents (antimicrobials) and anionic anticalculus agents, especially polyphosphates, have been found to be unstable in use, especially at the pHs normally required in an oral hygiene composition. Accordingly, it has not so far normally been possible to combine the excellent antiplaque action of cationic antimicrobials with the excellent anticalculus action of anionic species such as polyphosphates. Rather, it has been necessary either to use cationic anticalculus agents such as zinc ions, as described in U.S. Pat. No. 4,022,880 (Vinson et al) or non-cationic antimicrobials such as biphenolics and halogenated salicylanilides, as described in GB-A-2230187 (Colgate Palmolive).

This problem is reflected in GB-A-2230187 where it is stated at page 2, lines 11/18 that:

"Hitherto, the cationic antibacterial materials such as chlorhexidine, benzethonium chloride and cetyl pyridinium chloride have been the subject of greatest investigation as antibacterial antiplaque agents. However, in spite of their being used in conjunction with zinc anticalculus agent, they are not effective when used with anionic materials such as polyphosphate anticalculus agent".

U.S. Pat. No. 3,934,002 (Procter and Gamble) discloses an oral composition comprising a bis-biguanide antimicrobial agent and an anionic anti-calculus agent which inhibits the tendency of the bis-biguanide compound to produce a stain on oral surfaces. A surfactant, such as polyoxyethylene (20) sorbitan monoisostearate, may be included in the composition. However, it appears that the composition is not fully stabilised, since it is stated that where the bis-biguanide compound is not a water-insoluble compound having a solubility in water less than the corresponding salt of the bis-biguanide with the anti-calculus agent, then an excess of the anti-calculus agent must be used to neutralise the bis-biguanide compound, otherwise the two will react leaving insufficient free anti-calculus agent.

U.S. Pat. No. 4,323,551 (Procter and Gamble) discloses a mouthwash composition exhibiting plaque control/reduced staining tendencies comprising a quaternary annonium compound and a pyrophosphate salt and having a pH of from 7.0 to 9.5.

European Patent Publication No. 480812 (Colgate-Palmolive) discloses an oral composition comprising both a cationic antibacterial agent (such as chlorhexidine digluconate) and an anionic active agent (such as certain polyphosphates and polyphosphonates). The composition is stabilised by use of an effective amount of a betaine-type surfactant. The document states that "only the ampholyte betaine offers the window of opportunity wherein both precipitation inhibition and activity prevail". It is further stated that the betaine must be present in a quantity at least sufficient to prevent the precipitation of the bis-biguanide anionic agent salt.

It has now surprisingly been found that the amount of the betaine-type surfactant can be substantially reduced by including a non-ionic surfactant having a high HLB (hydrophilic/lipophilic balance).

Whilst betaine and betaine-type surfactants remain the surfactants of choice in the present invention, it is also possible to use alternative amphoteric surfactants.

Reducing the amount of betaine-type surfactant is desirable, since betaine-type surfactants have a strong taste which may not be well accepted by all users.

According to the present invention there is provided an oral hygiene composition comprising an effective amount of a substantially water soluble cationic antimicrobial agent or an orally acceptable salt thereof, an effective amount of a substantially water soluble anionic active agent or an orally acceptable salt thereof, and a stabilising combination of a non-ionic surfactant having a high hydrophilic/lipophilic balance and an amphoteric surfactant. The combination of surfactants used stabilises the composition, thus ensuring effective antimicrobial action and allowing the composition to be stored for long periods of time without deterioration.

The term 'anionic active agent' as used herein donates an anionic agent having anticalculus and/or antistaining properties.

Preferably the non-ionic surfactant has a hydrophilic/lipophilic balance of at least about 10, preferably between 13 and 18, suitably about 15.

Suitable non-ionic surfactants include silicone copolyols, fluoro surfactants, ethoxylated fatty alcohols and their derivatives, and ethoxylated vegetable oils. Polyoxyethylene sorbitan detergents (such as those available commercially under the trade name 'Tween') are particularly suitable, e.g. polyoxyethylene (20) sorbitan monopalmitate (available commercially under the trade name 'Tween' 20). Suitable vegetable oils include ethoxylated hydrogenated castor oil e.g. polyoxyethylene (40) hydrogenated castor oil (available commercially under the tradename 'Croduret 40'). It will be appreciated that blends comprising more than one non-ionic surfactant may be used if desired.

Suitable amphoteric surfactants for use in the composition are amine oxides, imidazolines, glycinates, amino propionates, and alpha-amino carboxylic acids, preferably betaine and/or derivatives thereof such as cocoamidopropyl betaine and the sulfobetaines. It will be appreciated that blends comprising more than one amphoteric surfactant may be used if desired.

In a preferred embodiment, the anionic active agent is an anticalculus agent such as a polyphosphate, preferably a pyrophosphate. The latter compound is a particularly effective anticalculus agent. Suitable pyrophosphates include disodium pyrophosphate, dipotassium pyrophosphate, tetrasodium pyrophosphate and tetrapotassiumpyrophosphate, and mixtures thereof. The preferred source of pyrophosphate is a mixture of tetrasodium pyrophosphate and tetrapotassium pyrophosphate. Suitably, the ratio of tetrasodium pyrophosphate to tetrapotassium pyrophosphate in such a mixture is 0:1 to 3:1, preferably 0:1 to 1:1. Preferably, tetrapotassium pyrophosphate is the predominant species.

Suitably, the cationic antimicrobial agent is a quaternary amine. Preferably, the antimicrobial agent is N-α-cocoyl-L- arginine ethyl ester (hereinafter referred to as "CAE"), suitably as the pyrollidone carboxylic acid salt, or 1,1'-hexamethylenebis [5-(p-chlorophenyl)biguanide, (hereinafter referred to as chlorhexidine) or an orally acceptable salt thereof, suitably the gluconate salt. However, it will be understood that alternative cationic antimicrobials (and orally acceptable salts thereof) such as amine fluorides, benzethonium chloride and cetyl pyridinium chloride and mixtures thereof may also be used if desired.

In a particularly preferred embodiment, the cationic antibacterial agent is chlorhexidine or an orally acceptable salt thereof such as the gluconate salt. Normally the use of chlorhexidine in oral products is seriously restricted by the propensity of this compound to stain pellicle and other protein-coated surfaces in the mouth. This problem is described, for example in EP-A-0161898 (Unilever PLC). However, it has now surprisingly been found that when chlorhexidine is included in a composition in accordance with the present invention, this undesirable staining is substantially reduced.

Thus, in a preferred form the invention provides an oral hygiene composition comprising an antimicrobial amount of chlorhexidine or an orally acceptable salt thereof, an anti-staining anionic active agent and both a non-ionic surfactant having a high hydrophilic/lipophilic balance and an amphoteric surfactant.

Suitably, the non-ionic and amphoteric surfactants are the preferred types described above.

Preferably, the anionic active agent is a polyphosphate, preferably pyrophosphate, since these agents have been found to give rise to particularly good resistance to staining.

The invention further provides the use of a polyphosphate species, especially a pyrophosphate species, and both a non-ionic surfactant having a high hydrophilic/lipophilic balance and an amphoteric surfactant (preferably betaine), to inhibit staining, especially protein staining, by chlorhexidine or salts thereof in an oral hygiene composition.

Suitably, the non-ionic and amphoteric surfactants are included in the composition to a total amount of from 0.1 to 10% by weight, preferably from 0.5 to 5% by weight, suitably about 2% by weight. Preferably, the non-ionic surfactant is included in an amount of from 0.05 to 2.5% by weight. Where the amphoteric surfactant is betaine or a betaine derivative, it is preferably included in an amount of from 0.01 to 8% by weight, suitably from 0.05 to 5% by weight, suitably from 0.1 to 3% by weight.

The corresponding thermodynamic activity of the surfactant combination is suitably from 0.01% to 5%, preferably from 0.1% to 2.5%, suitably about 1% by weight.

Suitably, the anionic anticalculus agent is included in an amount of from 0.25 to 10% by weight, preferably 1.5 to 7% by weight, suitably about 5% by weight.

Suitably, the cationic antimicrobial agent is included in an amount of from 0.01% to 5% by weight, preferably from 0.1% to 3% by weight.

The oral composition may be formulated for use in any form of interdental or periodontal treatment and may be in the form, for example, of a dentifrice, mouthwash, toothpowder, chewing gum, lozenge, mouthspray or impregnated floss.

Such compositions may contain conventional materials such as, for example, humectants, gelling agents, abrasives, fluoride sources, desensitising agents, flavourings, colourings, sweeteners, preservatives and structuring agents, and may also contain additional surfactants, anti-calculus agents and anti-plaque agents.

Suitable humectants include polyhydric alcohols such as xylitol, sorbitol, glycerol, propylene glycol and polyethylene glycols. Mixtures of glycerol and sorbitol are particularly effective. A humectant helps to prevent dentifrice compositions from hardening on exposure to air, and may also provide a moist feel, smooth texture, flowability, and a desirable sweetness in the mouth. Suitably, such humectants may comprise from about 0–85%, preferably from about 0–60% by weight of the oral hygiene composition.

As well as the particular surfactants specified above, compositions of the present invention may comprise one or more additional surfactants.

Suitable additional surfactants are water-soluble organic compounds, and may be nonionic, cationic or amphoteric species. The surfactant used should preferably be stable, able to form suds throughout a wide pH range, and able to produce a foam in use.

Suitable nonionic surfactants include the products of the condensation of alkylene oxide groups with aliphatic or alkylaromatic species, and may be, for example, polyethylene oxide condensates of alkyl phenols, ethylene oxide/propylene oxide copolymers (such as those available from BASF Wyandotte Chemical Corporation under the trade name 'Pluronic') ethylene oxide/ethylene diamine copolymers, ethylene oxide condensates of aliphatic alcohols, long chain tertiary amine oxides, long chain tertiary phosphine oxides, long chain dialkyl sulfoxides and mixtures thereof. Alternatives include ethoxylated sorbitan esters such as those available from ICI under the trade name "Tween".

Cationic surfactants are generally quaternary ammonium compounds having one $C_{8-18}$ alkyl chain and include, for example, lauryl trimethylammonium chloride, cetyl trimethylammonium bromide, di-isobutylphenoxy-ethoxyethyldimethyl-benzylammonium chloride, coconutalkyltrimethylammonium nitrite. Cetyl pyridinium fluoride. Also useful are benzyl ammonium chloride, benzyl dimethyl stearylammonium chloride, and tertiary amines having one $C_{1-18}$ hydrocarbon group and two (poly) oxyethylene groups.

Amphoteric surfactants are generally aliphatic secondary and tertiary amines comprising aliphatic species which may be branched or unbranched, and in which one of the aliphatic species is a $C_{8-18}$ species and the other contains an anionic hydrophilic group, for example, sulfonate, carboxylate, sulfate, phosphonate or phosphate. Examples of quaternary ammonium compounds are the quaternized imidazole derivatives available under the trade name 'Miranol' from the Miranol Chemical Company.

Structuring agents may be useful in, for example, dentifrices and gums to provide desirable textural properties and "mouthfeel". Suitable agents include natural gum binders such as gum tragacanth, xanthan gum, gum karaya and gum arabic, seaweed derivatives such as Irish moss and alginates, smectite clays such as bentonite or hectorite, carboxyvinyl polymers and water-soluble cellulose derivatives such as hydroxyethyl cellulose and sodium carboxymethyl cellulose. Improved texture may also be achieved, for example, by including colloidal magnesium aluminium silicate. Suitably, the structuring agent is included in an amount of from 0–5%, preferably 0–3% by weight of the oral hygiene composition.

Abrasives should preferably be capable of cleaning and/or polishing the teeth without causing harm to dental enamel or dentine. Suitable abrasives include the silica abrasives, such as hydrated silicas and silica gels, particularly silica xerogels such as those available under the trade name 'Syloid' from W.R. Grace and Company. Also suitable are precipitated silica materials such as those available under the trade name 'Zeodent' from J.M. Huber Corporation, and diatomaceous earths such as those available under the trade name 'Celite' from Johns-Manville Corporation.

Alternative abrasives include alumina, insoluble metaphosphates such as insoluble sodium metaphosphate, calcium carbonate, dicalcium phosphate (in dihydrate and anhydrous forms), calcium pyrophosphate (including β-phase calcium) polymethoxylates and particulate thermosetting polymerised resins such as, for example, ureas, melamine-ureas, melamine-formaldehydes, urea-formaldehydes, melamine-urea-formaldehydes, cross-linked epoxides, melamines, phenolics, and cross-linked polyesters. Suitably, abrasives are included in an amount of from 0–80%, preferably 0–60% by weight of the oral hygiene composition.

Fluoride sources suitable for use in oral hygiene compositions of the present invention include sodium fluoride, zinc fluoride, potassium fluoride, aluminium fluoride, lithium fluoride, sodium monofluorophosphate, acidulated phosphate fluoride, stannous fluoride, ammonium fluoride, ammonium bifluoride and amine fluoride.

Preferably, the fluoride source is present in an amount sufficient to provide from about 50 ppm to about 4,000 ppm fluoride ions in use. Inclusion of a fluoride source is beneficial, since fluoride ions are known to become incorporated into the hydroxyapatite of tooth enamel, thereby increasing the resistance of the enamel to decay. Inclusion of a fluoride source is also desirable when a polyphosphate anti-calculus agent is included, in order to inhibit the enzymic hydrolysis of such polyphosphates by salivary phosphatase enzymes.

Suitable desensitising agents include, for example, formaldehyde, potassium nitrate, tripotassium citrate, potassium chloride and strontium chloride (suitably as hexahydrate), strontium acetate (suitably as hemihydrate) and sodium citrate/Pluronic (Trade Name; see above) gel.

Flavouring agents may be added to increase palatability and may include, for example, oils of peppermint, spearmint, wintergreen, sassafras and clove. Sweetening agents may also be used, and these include D-tryptophan, saccharin, dextrose, aspartame, levulose, acesulfam, dihydrochalcones and sodium cyclamate. Typically, such flavouring agents are included in amounts of from 0–5%, preferably from 0–2% by weight of the oral hygiene composition. Colouring agents and pigments may be added to improve the visual appeal of the composition. Suitable colourants include dyes, such as FD & C blue No.1, D & C yellow No.10 and D & C yellow No.3. A suitable and commonly used pigment is titanium dioxide, which provides a strong white colour.

The composition may also comprise alcohol. This component is particularly useful in mouthwash formulations, where it may be used to solubilise components which have low solubility in water.

In addition to the cationic antimicrobial agent specified above the compositions of the invention may include a further antimicrobial agent as a preservative and/or antiplaque agent. Suitable antimicrobial agents include zinc salts (such as zinc citrate) bromochlorophene, hexachlorophene, salicylanilides, and triclosan. Enzymic systems providing a source of a natural biocide may be used as alternatives to or in combination with the additional biocides listed. For example, a system comprising lactoperoxidase and glucose oxidase may be used to generate antimicrobial amounts of hydrogen peroxide in the presence of glucose, water and oxygen.

As well as the anionic anticalculus agent specified above, compositions of the invention may comprise additional anticalculus agents such as zinc salts (e.g. zinc citrate and zinc chloride).

Particularly suitable oral compositions are those in the form of a mouthwash or toothpaste.

According to a further aspect of the invention, there is provided a method of cleaning the mouth for cosmetic purposes by oral application of any oral hygiene composition as defined above.

In a further aspect, the invention provides a method of treating or preventing gum disease or dental caries by oral application of any oral hygiene composition as defined above.

In a further aspect, there is provided the use of any oral hygiene composition as defined above in the treatment or prevention of gum disease or dental caries.

In a further aspect, there is provided the use of any oral hygiene composition as defined above in the manufacture of a medicament for the treatment or prevention of gum disease or dental caries.

The invention also provides the use of a non-ionic surfactant having a high hydrophilic/lipophilic balance (suitably at least 10), and an amphoteric surfactant, (especially betaine or cocoamidopropyl betaine), to stabilise an oral hygiene composition comprising a water-soluble cationic antimicrobial agent (especially CAE or chlorhexidine) and a water-soluble anionic anticalculus agent (especially pyrophosphate).

The nature of the oral hygiene compositions of the present invention is illustrated by the following Tests and Examples.

COMPARATIVE TEST A

Test solutions A to J were formulated as shown in Table 1 each at a pH of approximately 7. In each case the pyrophosphate was added last to a precursor solution comprising each of the other components.

Table 1

| | % by weight (balance = water) | | | | | |
|---|---|---|---|---|---|---|
| Solution | Chlorhexidine gluconate (added as 20% solution) | Tego betaine ZF | 'Tween 20' non-ionic surfactant | 'Croduret 40' non-ionic surfactant | Tetrasodium pyrophosphate (added as 2.5% solution at pH7) | Observations |
| A | 0.124 | 0.257 | — | — | 0.125 | precipitate formed on addition of pyrophosphate |

Table 1-continued

| | % by weight (balance = water) | | | | | |
|---|---|---|---|---|---|---|
| Solution | Chlorhexidine gluconate (added as 20% solution) | Tego betaine ZF | 'Tween 20' non-ionic surfactant | 'Croduret 40' non-ionic surfactant | Tetrasodium pyrophosphate (added as 2.5% solution at pH7) | Observations |
| B | 0.124 | 0.415 | — | — | 0.125 | precipitate formed on addition of pyrophosphate |
| C | 0.124 | 0.512 | — | — | 0.125 | precipitate formed on addition of pyrophosphate |
| D | 0.124 | 0.765 | — | — | 0.125 | solution clear on addition of pyrophosphate |
| E | 0.124 | 0.314 | 0.2 | 0.2 | 0.125 | solution cloudy on addition of pyrophosphate but cleared on standing |
| F | 0.124 | 0.415 | 0.2 | 0.2 | 0.125 | solution clear on addition of pyrophosphate |
| G | 0.124 | — | 0.2 | 0.2 | 0.125 | solution cloudy on addition of pyrophosphate and did not clear on standing |
| H | 0.124 | — | 0.4 | 0.4 | 0.125 | solution cloudy on addition of pyrophosphate and did not clear on standing |
| J | 0.124 | — | 0.5 | 0.5 | 0.125 | solution clear on addition of pyrophosphate |

COMPARATIVE TEST B

Solutions D, E, F, H and J from Comparative Test A above, were tested for substantivity and antiplaque activity as follows:

Thin strips of perspex coated with hyroxyapatite were used as 'artificial tooth' surfaces. The strips were soaked in a solution designed to simulate (stimulated) human saliva ('artificial' saliva) and then soaked in the solution under test for 2 minutes. The strips were then transferred to fresh 'artificial' saliva for 30 minutes to mimic the effects of long term salivary flow, and then transferred to an incubation medium containing tryptone, yeast extract, sucrose and pooled freshly collected human plaque in which they were incubated at room temperature for 5 hours. The strips were then transferred to distilled water and ultrasonically treated to remove the plaque organisms. The optical density at 570 nm of the resulting plaque suspension was used to estimate the percentage reduction in plaque growth compared to plaque growth on test strips exposed to a control composition of 'artificial' saliva and water. Each solution was tested on five strips and the mean of the respective absorbance readings was taken.

The percentage reductions in amount of plaque present compared to the negative control (comprising only 'artificial' saliva and water) are shown in Table 2. Non-parametric Kruskal-Wallis analysis of variance, followed by a multiple comparison technique (using a significance level of p less than 0.01), shows that of the test solutions there was a statistically significant reduction in plaque level on strips treated with solution E only. A positive control (comprising 0.124% chlorhexidine only) gave plaque reduction of 47.1% (which was statistically significant).

TABLE 2

| Solution | % reduction in plaque growth | Statistical Significance |
|---|---|---|
| D | 39.2 | No |
| E | 46.3 | Yes |
| F | 23.8 | No |
| H | 34.6 | No |
| J | 37.9 | No |

As a further positive control, the antiplaque assay described was carried out using the commercial mouthwash formulation available under the tradename 'Corsodyl'. This gave a plaque reduction of 49.2% (which was statistically significant).

FORMULATION EXAMPLE 1

A mouthwash formulation was prepared to the following composition:

| Component | Concentration (% w/w) |
| --- | --- |
| CAE | 0.48 |
| Cocamidopropyl betaine (30% active) | 2.94 |
| Tetrasodium pyrophosphate | 1.62 |
| Tetropotassium pyrophosphate | 2.38 |
| Propylene glycol | 5.0 |
| Sorbitol (70% solution) | 10.0 |
| Polyoxyethylene (20) sorbitan monolaurate | 0.15 |
| Polyoxyethylene (40) hydrogenated castor oil | 0.15 |
| Hydrochloric acid (1M) | 2.59 |
| Citric acid monohydrate | 0.81 |
| Sodium saccharin | 0.03 |
| Sodium fluoride | 0.05 |
| Flavour | 0.17 |
| Colour | 0.04 |
| Water | to 100% |

METHOD

1. The major components—CAE, cocoamidopropyl betaine, pyrophosphates and hydrochloric acid—were mixed in aqueous solution in approximately half the final volume of water.

2. The flavour was mixed into the propylene glycol.

3. The polyoxyethylene based emulsifiers were dissolved into water with warming.

4. The propylene glycol and emulsifier solutions were mixed and added to the bulk.

5. The remaining other components were added with constant stirring and the final volume was made up to 100% with water.

The product was clear with a pH of 6.3.

FORMULATION EXAMPLE 2

A mouthwash formulation was prepared to the following composition:

| Component | Concentration (% w/w) |
| --- | --- |
| Polyoxyethylene (40) hydrogenated castor oil | 0.25 |
| Chlorhexidine gluconate solution (BP) (20%) | 1.0 |
| Cocoamidopropyl betaine (30% active) | 1.0 |
| Tetrasodium pyrophosphate | 2.50 |
| Tetrapotassium pyrophosphate | 2.50 |
| Citric acid monohydrate | 1.50 |
| Water | to 100% |

METHOD

1. The polyoxyethylene (40) hydrogenated castor oil was dissolved in 40/75 of the water with warming and stirring, and then cooled.

2. The chlorhexidine gluconate and cocoamidyl betaine were separately added to (1).

3. The tetrasodium and tetrapotassium pyrophosphate was dissolved in the remainder of the water, with warming and stirring, and then cooled.

4. The product from (3) was added to the product from (2) with stirring.

5. The citric acid monohydrate was added to the product from (4) with stirring.

6. The pH was checked (approx. 6.5) and the product was made up to 100% with water.

FORMULATION EXAMPLE 3

A mouthwash formulation was prepared to the following composition:

| Component | % w/w |
| --- | --- |
| Polyoxyethylene (40) hydrogenated castor oil | 0.75 |
| Polyoxyethylene (20) sorbitan monolaurate | 0.75 |
| Cocoamidopropylbetaine (30% active) | 0.50 |
| Propylene glycol | 4.0 |
| Sorbitol (70% solution) | 1.0 |
| Sodium saccharin | 0.025 |
| Flavour | 0.015 |
| Sorbic acid | 0.1 |
| Chlorhexidine gluconate solution B.P. (20%) | 1.0 |
| Tetrapotassium pyrophosphate | 1.65 |
| Tetrasodium pyrophosphate | 1.65 |
| Citric acid | 1.14 |
| Water | to 100% |

METHOD

1. The surfactant blend was dissolved in warm water and sodium saccharin was added. The mixture was stirred until clear.

2. The propylene glycol, sorbitol, flavour and sorbic acid were mixed together and then added to bulk with stirring.

3. The chlorhexidine gluconate solution was stirred in to the mixture from (2).

4. A solution of the pyrophosphate was prepared with warming, cooled and stirred into the bulk.

5. The pH was checked (approx. 6.0) and made up to 100% with water.

This formulation was tested in the anti-plaque assay described in Comparative Test B above and shown to give a plaque reduction of 47.5% (which was statistically significant).

The formulation was also tested using procedures similar to those outlined Jenkins et al (Clin Periodontol 17: 698–701, 1990). Saliva samples were taken at intervals after using the formulation. Each sample was incubated anaerobically for 48 hours at dilutions between $10^{-3}$ and $10^{-6}$. Colony forming units/ml saliva sample were calculated from those dilutions exhibiting 10–30 colonies per plate. The results showed that the formulation reduced salivary counts of anaerobic bacteria significantly and that this suppression was maintained over the 6 hour test period.

We claim:

1. A stable oral hygiene composition comprising:
  a) an effective amount of at least one substantially water soluble cationic anti-microbial agent, or an orally acceptable salt thereof;
  b) an effective amount of at least one polyphosphate which is effective against at least one of calculus and stain, or an orally acceptable salt thereof;
  c) at least one non-ionic surfactant having a hydrophilic/lipophilic balance of at least about 10; and
  d) at least one amphoteric surfactant comprising betaine, or a derivative thereof.

2. A composition according to claim 1, wherein said non-ionic surfactant has a hydrophilic/lipophilic balance of between 13 and 18.

3. A composition according to claim 1, wherein said at least one non-ionic surfactant is selected from a group consisting of silicone copolyol, fluoro surfactant, ethoxylated fatty alcohol, ethoxylated vegetable oil and polyoxyethylene sorbitan detergent.

4. A composition according to claim 1, wherein the polyphosphate is an alkali metal pyrophosphate.

5. A composition according to claim 1, wherein said at least one substantially water soluble cationic anti-microbial agent is chlorhexidine, or an orally acceptable salt thereof.

6. A composition according to claim 1, wherein surfactants (c) and (d) comprise 0.1 to 10% by weight of said composition.

7. A composition according to claim 1, wherein said at least one amphoteric surfactant is present in an amount of from 0.05 to 5% by weight of said composition.

8. A composition according to claim 1, wherein said at least one non-ionic surfactant is present in an amount of from 0.05 to 2.5% by weight of said composition.

9. A composition according to claim 1, wherein said at least one polyphosphate is present in an amount of from 0.25 to 10% by weight of said composition.

10. A composition according to claim 1, wherein said at least one substantially water soluble cationic anti-microbial agent is present in an amount of from 0.01 to 5% by weight of said composition.

11. A method of cleaning a mouth for cosmetic purposes, comprising orally applying the oral hygiene composition according to claim 1.

12. A method of treatment or prophylaxis of at least one of gum disease and dental caries, said method comprising orally applying the oral hygiene composition according to claim 1.

13. A method of stabilizing an oral hygiene composition comprising:

a) an effective amount of at least one substantially water soluble cationic anti-microbial agent, or an orally acceptable salt thereof; and b) an effective amount of at least one polyphosphate which is effective against at least one of calculus and stain;

said method comprising combining the oral hygiene composition with (i) a non-ionic surfactant having a hydrophilic/lipophilic balance of at least about 10; and (ii) at least one amphoteric surfactant selected from a group comprising betaine, or a derivative thereof, to produce a stable oral hygiene composition.

* * * * *